United States Patent [19]

Isner

[11] Patent Number: 5,368,034
[45] Date of Patent: Nov. 29, 1994

[54] METHOD AND APPARATUS FOR THROMBOLYTIC THERAPY

[75] Inventor: Jeffrey M. Isner, Weston, Mass.

[73] Assignee: Boston Scientific Corporation, Watertown, Mass.

[21] Appl. No.: 939,896

[22] Filed: Sep. 4, 1992

[51] Int. Cl.⁵ ............................................. A61B 5/0215
[52] U.S. Cl. ......................... 128/660.03; 128/691; 128/661.09; 128/662.04
[58] Field of Search ............... 128/662.04, 662.06, 128/662.03, 661.08, 661.09, 661.10, 660.03, 691, 903

[56] References Cited

U.S. PATENT DOCUMENTS

| | | | |
|---|---|---|---|
| 3,646,606 | 2/1972 | Buxton et al. | 128/903 |
| 4,424,814 | 1/1984 | Secunda | 128/663 |
| 4,529,397 | 7/1985 | Hennemuth et al. | 604/4 |
| 4,587,972 | 5/1986 | Morantte, Jr. | 128/660.03 |
| 4,627,419 | 12/1986 | Hills | 128/1 |
| 5,014,715 | 5/1991 | Chapolini | 128/691 |
| 5,022,399 | 6/1991 | Biegeleisen | 128/660.03 |
| 5,058,595 | 10/1991 | Kern | 128/662.06 |
| 5,078,148 | 1/1992 | Nassi et al. | 128/661.10 |

*Primary Examiner*—William E. Kamm
*Assistant Examiner*—George Manuel
*Attorney, Agent, or Firm*—Pearson & Pearson

[57] ABSTRACT

A method and system for facilitating thrombolytic therapy includes a perfusion tube, in the form of an infusion guidewire or catheter, for delivering a lytic agent at a thrombosis. The perfusion tube includes, as an integral part thereof, at its distal end a sensor that connects to monitoring and announcing circuit. The monitoring and announcing circuit may include local and remote audio and visual announcing mechanisms for indicating the existence of blood flow above a predetermined minimum flow rate thereby to indicate lysis.

25 Claims, 4 Drawing Sheets

METHOD AND APPARATUS FOR THROMBOLYTIC THERAPY

BACKGROUND OF THE INVENTION

1. Field of the Invention

This invention generally relates to a method and apparatus for facilitating lytic therapy and more specifically to a method and apparatus for reperfusing a vessel occluded by a thrombosis by means of thrombolytic therapy.

2. Description of Related Art

Thrombolytic therapy is a form of lytic therapy that involves the infusion of a thrombolytic agent for dissolving a thrombosis and reperfusing a vessel. The therapy involves the surgical introduction of a perfusion tube, such as a catheter or infusion guidewire, into a patient. After a distal end of the perfusion tube is positioned in or proximate the thrombosis, the infusion of a lytic agent, such as urokinase, begins. Sometimes this infusion may be preceded by the injection of a bolus of another lytic agent, such as streptokinase, through the infusion tube.

Infusion continues for some interval of time. Intervals ranging from several hours to a day are common. Angiographic or other similar diagnostic imaging techniques are used periodically during the infusion. These techniques monitor the effectiveness of the therapy and determine clot lysis by the onset of blood flow through the vessel. If lysis has occurred, the infusion terminates. Otherwise the infusion continues until the next diagnostic imaging session. This cycle of infusion and diagnostic imaging continues until lysis occurs.

This procedure has several disadvantages. Both the introduction of the catheter and the monitoring of the effectiveness of the therapy require the use of surgical facilities and attendance of medical personnel for the duration of the therapy. Normally the infusion is terminated during any diagnostic imaging session. Diagnostic imaging is conducted periodically with intervals of twenty minutes to two hours being typical. Consequently, it is difficult to determine the precise time at which the infusion of the lytic agent should terminate. If a given diagnostic imaging session discloses that lysis is complete, it can only be said that lysis occurred some time after the prior diagnostic imaging session. Patient tolerance and facility demands may limit the frequency of such diagnostic imaging sessions. Any delay between lysis and the termination of infusion may involve the needless administration of the lytic agent.

An improved method and system for thrombolytic therapy and other forms of lytic therapy that overcome these problems is needed. It would be particularly desirable to develop a method and system for limiting the infusion of a lytic agent precisely to the interval and amount required for lysis. It also would be desirable to develop an alternative method of determining the onset of blood flow through a reperfused vessel that reduces patient trauma and reduces the utilization of surgical resources.

The following patents disclose medical diagnostic monitoring apparatus for measuring blood flow in vivo using ultrasonic measurement techniques:

U.S. Pat. No. 4,582,067 (1986) Silverstein
U.S. Pat. No. 4,637,401 (1987) Johnston
U.S. Pat. No. 4,733,669 (1988) Segal
U.S. Pat. No. 4,771,788 (1988) Millar
U.S. Pat. No. 4,869,263 (1989) Segal et al
U.S. Pat. No. 4,947,852 (1990) Nassi et al The Silverstein patent discloses a catheter used with an endoscope. The catheter supports a Doppler crystal transducer at its distal end. This catheter is dedicated to measuring in vivo blood flow for the purpose of identifying and monitoring intracorporeal biological structures for medical diagnosis.

The Johnston patent discloses diagnostic apparatus for measuring volumetric blood flow. The apparatus includes a Doppler transducer at a distal end of a catheter for being located in a vessel. Measurements are taken when a proximally located balloon is deflated or inflated. The measured flow rates under these balloon conditions is then converted into a volumetric flow rate.

Segal discloses a catheter with a Doppler crystal transducer adapted for measuring flow in a vessel with improved accuracy. The apparatus includes a wire that coacts with a vessel wall to position the Doppler transducer at an opposite vessel wall thereby to assure measurement at a predetermined position in the vessel.

In accordance with the Millar patent apparatus for measuring blood flow includes a guidewire with a central lumen that carries, in one embodiment, a steering wire. A Doppler crystal transducer is located at the distal end. This apparatus is adapted for measuring blood flow at various positions along an arterial tree. It is suggested that the lumen could be used for introducing chemicals or fluids, such as aneurism dye, into the blood stream.

The Segal et al patent discloses a catheter with multiple lumens and a distal ultrasonic transducer for measuring cardiac output. Readings of the transducer signals are taken when a balloon is inflated to different diameters.

Nassi et al disclose a catheter with multiple lumens that supports two transducers at its distal end. One of the lumens is identified as a right atrial pressure and injectate lumen. Nassi et al also disclose a console that displays blood flow and vessel diameter measurements. This apparatus provides an alarm if the blood flow or vessel diameter exceeds a minimum or maximum limit.

Although ultrasonic blood flow monitors in various forms have existed for over 20 years, they have been used as diagnostic tools. Even a suggestion of using the apparatus to inject a dye or the like occurs in the context of a diagnostic procedure. As these devices have matured, they have become more accurate, more complex and more expensive. They have not been adopted for therapeutic applications such as monitoring the onset of blood flow during thrombolytic therapy. Consequently, thrombolytic therapy has continued to rely on angiographic and other diagnostic imaging techniques notwithstanding the potential for additional patient trauma and demands on medical resources.

SUMMARY

Therefore it is an object of this invention to provide a method and apparatus for use in reperfusing a vessel that incorporates blood flow monitoring as an integral part thereof.

Another object of this invention is to provide a method and apparatus for reperfusion that incorporates monitoring the onset of blood flow in response to lysis.

Another object of this invention is to provide a method and apparatus for thrombolytic therapy that enables the termination of infusion immediately upon the onset of blood flow through a vessel.

Still another object of this invention is to provide a method and apparatus for reperfusion therapy that is less traumatic to the patient.

Still another object of this invention is to provide a method and apparatus for reperfusion therapy that is less traumatic to the patient and reduces the impact on the surgical resources of a health care center.

In accordance with one aspect of this invention, the distal end of a reperfusion tube is located in an occluded vessel for enabling the introduction of a reperfusion or lytic agent. A sensor associated with a blood flow monitor mounts at the distal end of the perfusion tube. This sensor generates a flow rate signal in response to blood flow through the vessel. The measured flow is compared with a predetermined flow rate value. An announcing circuit produces a signal that indicates the onset of a predetermined flow rate through the vessel when the measured flow rate exceeds the predetermined flow rate. This announcement provides an immediate indication of lysis and enables the infusion process to be terminated forthwith.

In accordance with another aspect of this invention, the reperfusion of a vessel occluded by a thrombosis by means of a lytic agent includes positioning the distal end of a perfusion tube with a flow sensor in the vessel in or proximate the thrombosis. A lytic agent is administered through the perfusion tube from its proximal end. The flow sensor continuously monitors blood flow rate. When the measured blood flow rate exceeds a predetermined rate, the onset of blood flow is announced and the administration of the lytic agent can be terminated.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
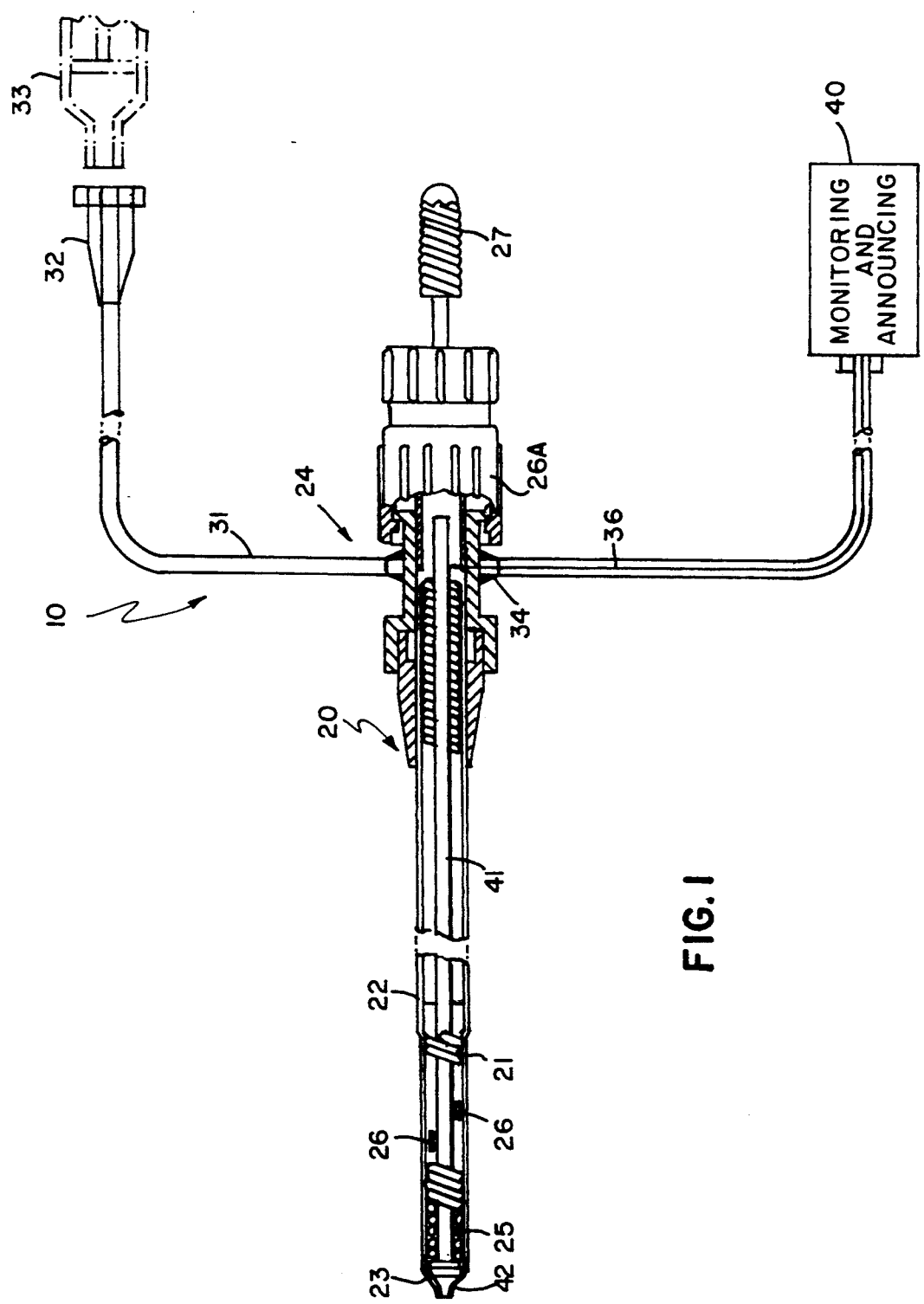
FIG. 1 is a view of apparatus constructed in accordance with this invention.

FIG. 1 discloses reperfusion apparatus 10 with a perfusion tube in the form of an infusion guidewire 20 having a tubular coil 21 and an outer sheath 22. The coil 21 and sheath 22 extend between a distal end 23 and a proximal end 24 defining a continuous lumen 25. A plurality of weep holes 26 are formed through the sheath 22 near the distal end 23. A fitting 26A at the proximal end acts as a clamping device for an obturator 27. The fitting 26A also includes a tee-connection for receiving a tube 31 from a syringe fitting 32. A syringe 33 or similar device connects to the fitting 32 to administer a lytic agent through the tube 31 and the lumen 25 into the area of a thrombosis through the distal end 23 and the weep holes 26.

Another tee-fitting 34 on the fitting 26A includes tubing 35 for carrying conductors 36 to a monitoring and announcing circuit 40. These conductors 36 extend through the tube 35, the fitting 34 and the lumen 25 to a Doppler crystal transducer 42 at the distal end of the guidewire 20.

Figure 2:
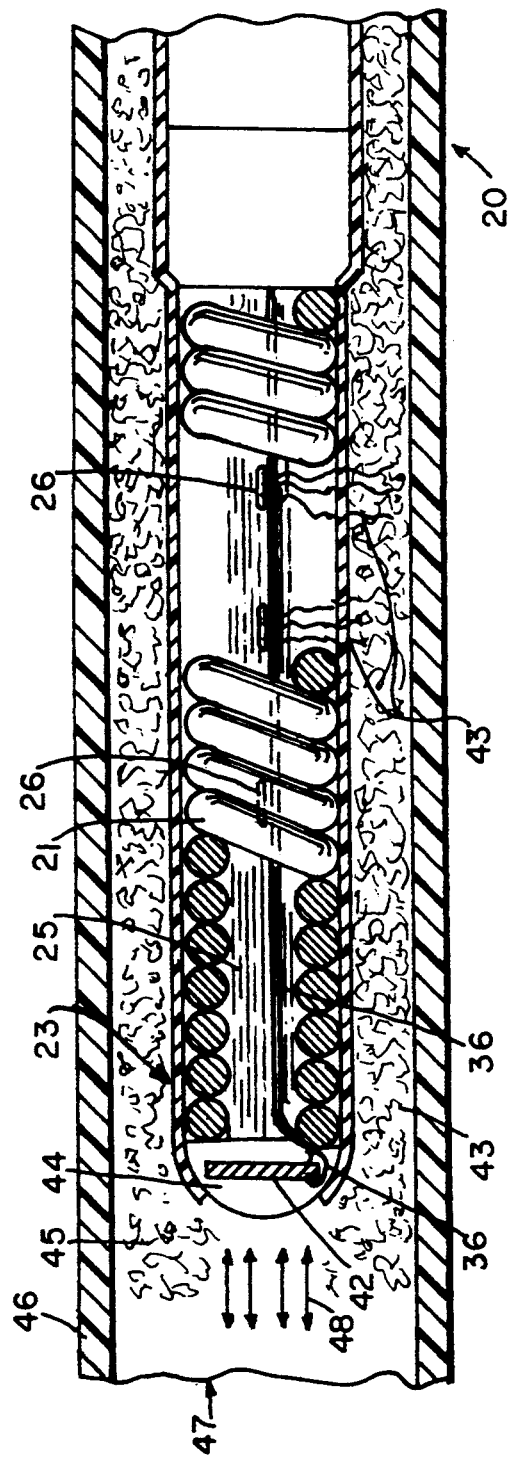
FIG. 2 is an enlarged detailed view of the apparatus shown in FIG. 1.

FIG. 2 discloses the distal end 23 of the guidewire 20 in a vessel occluded by a thrombosis. More specifically, a lytic agent 43 supplied from the syringe 33 or similar device shown in FIG. 1 fills the lumen 25. As pressure is applied from the proximal end of the guidewire 20, the lytic agent 43, blocked by an end plug 44, sprays through the weep holes 26. Thus the lytic agent is directed toward and into contact with the thrombosis 45 that extends across vessel walls 46 and occludes the vessel 47. As known the lytic agent 43 acts over time to dissolve the thrombosis 45. Intervals from several hours to a day are common.

Figure 3:
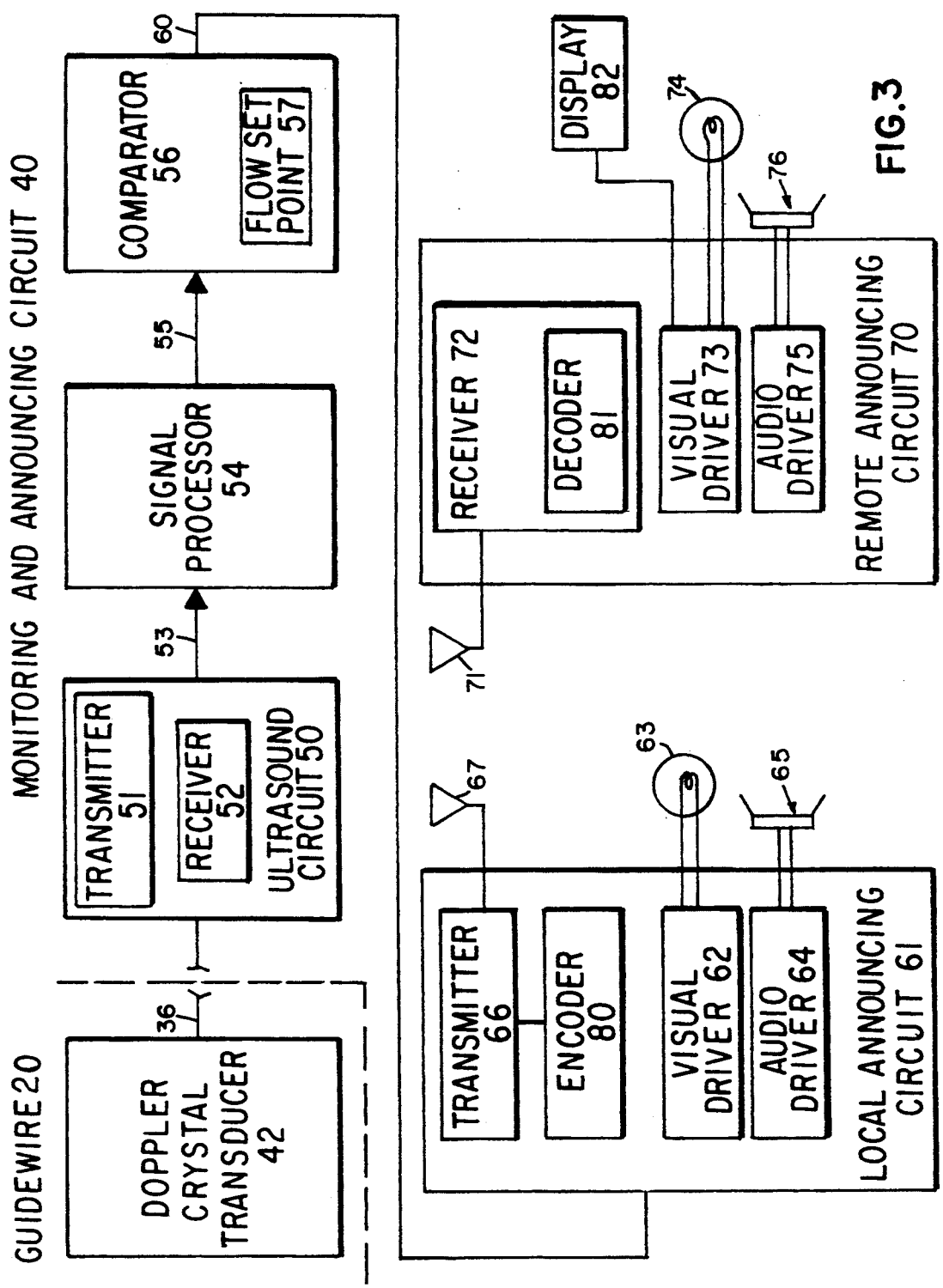
FIG. 3 is a schematic diagram of monitoring and announcing circuitry in accordance with this invention.

In accordance with this invention the guidewire 20 includes, as an integral component, a flow monitoring device that includes an ultrasound circuit 50 as shown in FIG. 3. The ultrasound circuit 50 includes a transmitter 51 and a receiver 52 that can operate in either a pulse-echo or continuous mode. FIG. 2 depicts a single transducer 42 traversing the lumen 25. Such a single transducer 42 would operate in a pulse-echo mode. As known in the art and shown in FIG. 3, the transmitter 51 would, in this mode, generate a succession of spaced pulses and the receiver 52 would monitor the received signal intermediate the pulses. In FIG. 2, these pulses and returned energy pass through the end plug 44 and are represented by arrows 48.

As shown in FIG. 3, a conductive path 53, that may comprise one or more conductors, transfers the received signals to a signal processor 54. Typically the signal processor 54 monitors any phase shift in the received signal and uses Doppler techniques to quantify the rate of blood flow through the vessel. The resulting blood flow rate signal appears on a conductive path 55 to a comparator 56. The comparator 56 analyzes the magnitude of the blood flow rate signal from the path 55 with a predetermined flow rate value provided by a flow set point circuit 57. That flow rate set point represents flow rates from zero to some upper limit that positively indicates that lysis is complete. The comparator 56 produces an output signal on a conductive path 60 indicating the onset of blood flow and the completion of lysis. The conductive path 60 conveys this signal to a local announcing circuit 61.

The local announcing circuit 61 can take any of several forms and typically will be located at the patient's site. For example, the local announcing circuit 61 may merely comprise a visual driver circuit 62 that energizes a lamp 63 when the comparator 56 generates a signal on the conductive path 60. Alternatively, or in addition, the local announcing circuit 61 can include an audio driver circuit 64 in a form of an oscillator that turns on in response to the signal from the comparator 56 to produce an audible tone or series of audible tones from a speaker 65. Either of these circuits, taken individually or in combination, provide an announcement of the onset of blood flow through the vessel. The combination of a visual and/or audible announcement then direct personnel in the vicinity to an appropriate patient.

It is also possible for the local announcing circuit 61 to include, as an alternative or in addition, a low power RF transmitter 66 with a transmitting antenna 67 for activating a remote, beeper-like, announcing circuit 70.

More specifically, a receiving antenna 71 and a receiver 72 would detect any transmission from the transmitter 66. Then the receiver 72 could energize a visual driver 73 and lamp 74 and/or an audio driver 75 and speaker 76 included in the remote announcing circuit 70.

If several patients are under treatment simultaneously, the local announcing circuit 61 could include an encoder 80 for identifying a particular hospital site or patient. In that circumstance the receiver 72 could include a decoder 81 for limiting the response of the remote announcing circuit 70 to signals for a particular patient. Alternatively, the remote announcing circuit 70 could identify the patient or site on an alphanumeric display 82.

The inclusion of the transmitter 66 and the local announcing circuit 61 and remote announcing circuit 70 in the overall system enables a remote announcement of the onset of blood flow to a physician or nurse. Thus, the physician or nurse can attend to other patients and priorities while the infusion continues.

As will now be apparent, the apparatus shown in FIGS. 1 through 3 facilitates thrombolytic and similar therapies. As the sensor 42 is an integral part of the perfusion tube constituted by the guidewire 20 in FIG. 1, there is no requirement for the introduction for any separate catheter or guidewire solely for the purpose of monitoring blood flow. As the monitor in accordance with this invention provides an essentially immediate announcement of the onset of blood flow, the infusion process can be terminated when lysis is complete. There is no need to continue the infusion until a next angiographic or related diagnostic imaging session. Indeed, there is no need for such diagnostic imaging sessions at all during infusion. Consequently a patient can be transferred to a bed outside the surgical facilities during the infusion without any need for repeated returns to and the use of the surgical resources of the hospital. Consequently, patient trauma lessens and use of surgical resources can be reduced.

Figure 4:
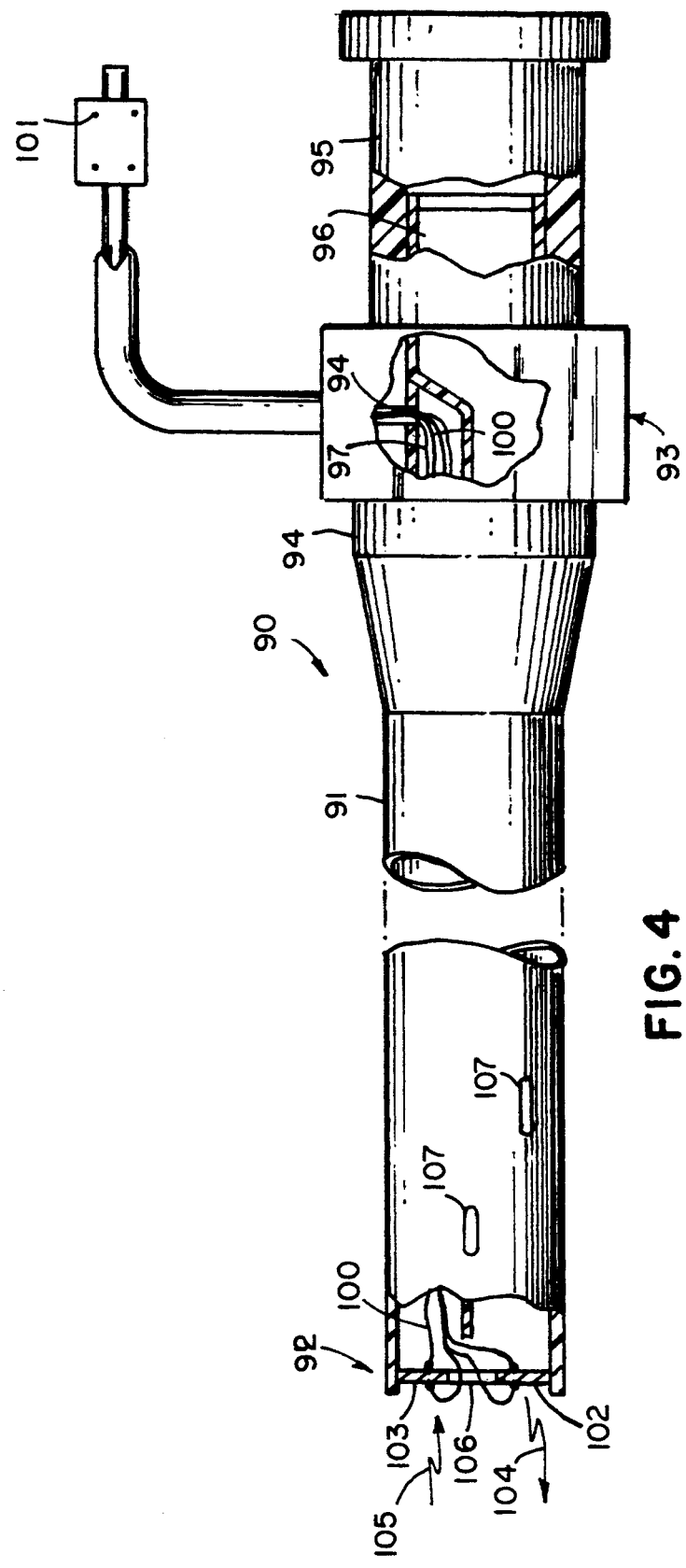
FIG. 4 is an alternative embodiment of apparatus for reperfusion therapy incorporating this invention.

FIG. 4 discloses an alternative to the guidewire 20 shown in FIG. 1. More specifically, FIG. 4 discloses, as a perfusion tube, a catheter structure 90. A catheter tube 91 that extends between a distal end 92 and a proximal end 93 defined by an end fitting 94 having a Leur-lock or related syringe fitting 95. In this particular embodiment, the catheter tube 91 has two lumens as an example of a multiple lumen catheter. A first, or major, lumen 96 extends throughout the length of the catheter tube 91. At the proximal end 93, the lumen 96 communicates with the syringe fitting 95 thereby to serve as a conduit for the lytic agent. The second lumen 97 extends from the distal end 92 to the end fitting 94 and provides a passage for conductors 100.

The end fitting 94 directs the conductors 100 to an electrical connector 101 for connection to a complementary fitting from a mounting and announcing circuit like the circuit 40 in FIGS. 1 and 3. At the distal end 92, the conductors 100 attach, in this embodiment, to a transmitting Doppler crystal 102 and a receiving Doppler crystal 103. This particular embodiment allows a transmitter analogous to the transmitter 51 in FIG. 3 to generate ultrasonic energy continuously to be radiated from the transducer 102 as represented by arrow 104. Reflected ultrasonic energy, represented by arrow 105 impinges the receiving transducer 103 with corresponding signals transferring to circuitry analogous to the receiver 52 shown in FIG. 3. Modifications to the circuitry shown in FIG. 3 for accommodating the continuous operating mode are well known.

The catheter 90 in FIG. 4 additionally has an open end 106 formed by the Doppler crystals 102 and 103 to provide a passage 106 for the lytic agent. The catheter 91 may also include weep holes 107 for allowing a radial distribution of the lytic agent.

As will be apparent the Doppler crystal 42 in FIG. 1 and the Doppler crystals 102 and 103 in FIG. 4 are disposed transversely to the axis of the guidewire 20 and the catheter 91 respectively. Consequently ultrasonic energy radiates from the transducer 42 or the transducer 102 essentially parallel to the axis of the guidewire 20 or catheter 91 (to the left or downstream in FIGS. 2 and 4). When the thrombosis 45 in FIG. 2 dissolves, blood flow begins and the resulting flow will produce a Doppler shift in the signals directed to the receiver 52 in FIG. 3.

In use, a perfusion tube in the form of the guidewire 20 in FIGS. 1 and 2 or the catheter 90 in FIG. 4 is directed into an occluded vessel such as vessel 47 shown in FIG. 2. The distal end is positioned in the thrombosis 43. The monitoring and announcing circuit 40 of FIG. 3 is energized and the infusion of a lytic agent begins. Monitoring continues simultaneously with the infusion. There is no necessity for interrupting the infusion to monitor the effectiveness of the therapy. When lysis is complete and the thrombosis dissolves, the circuitry in FIG. 3 immediately detects and announces the resumption of blood flow. It can perform that announcement either locally to the patient or to medical personnel who are provided with a remote announcing circuit 70 that would typically be in the form of a conventional beeper signalling device.

Therefore in accordance with this invention, a simple circuit can be incorporated with Doppler crystal transducers for providing continuous monitoring of blood flow concurrently with infusion. It will be apparent from the foregoing description that a number of variations and modifications can be made to the specifically disclosed embodiments. For example, FIGS. 1 and 2 disclose a single lumen guidewire with the conductors extending through the lumen. The conductors might be located externally to the lumen or intermediate the sheath 22 and coil 21. Either of the specific embodiments of FIGS. 1 or 4 could include a continuous mode ultrasonic monitor or a pulse-echo mode ultrasonic monitor. Doppler signal processing has been disclosed. Other methods of signal analysis might be used for deriving a signal that would indicate the onset of blood flow. Similarly, methods for measuring the onset of blood flow using pressure detection or other techniques could be substituted for the disclosed ultrasonic technique. Remote announcing circuits may or may not be used. When used, remote announcing circuits might be configured to respond to different encoded transmissions in order that a single remote announcing circuit 70 could identify any of several patients undergoing infusion therapy. It is also possible that the local announcing circuits 61 could be constructed to work with conventional beeper circuits through telephone or related connections.

Thus, although this invention has been disclosed in terms of certain embodiments, it will be apparent that many modifications can be made to the disclosed apparatus without departing from the invention. It is the intent of the appended claims to cover all such variations and modifications as come within the true spirit and scope of this invention.

What is claimed as new and desired to be secured by Letters Patent of the United States is:

1. A system for reperfusing an occluded vessel comprising:
   A. perfusion tube means having a proximal end and having a distal end for location in the vessel for enabling the introduction of a reperfusion agent to the occluded vessel,
   B. flow monitoring means including sensor means mounted to said perfusion tube means at said distal end thereof for generating a flow rate signal in response to blood flow through the vessel parallel to and past said perfusion tube means,
   C. comparing means for comparing the value of the flow rate signal with a set point signal representing a predetermined flow rate, and
   D. announcing means connected to said comparing means for announcing a flow rate signal that exceeds the predetermined flow rate thereby to announce the onset of blood flow through the vessel.

2. A system as recited in claim 1 wherein said sensor means comprises ultrasound transducer means at the distal end of said infusion tube and said monitoring means additionally includes signal processing means for converting signals from said transducer means into the flow rate signal for said comparing means and conductor means intermediate said transducer means and said signal processing means.

3. A system as recited in claim 2 wherein transducer means includes a Doppler crystal means for transmitting signals in response to blood parallel said perfusion tube means and said signal processing means includes means for energizing said Doppler crystal means and for receiving signals therefrom.

4. A system as recited in claim 3 wherein said Doppler crystal means includes first and second crystal means and said signal processing means includes means for continuously driving said first crystal means and means for receiving signals from the second crystal means.

5. A system as recited in claim 3 wherein said signal processing means includes means for transmitting pulses in succession to said Doppler crystal means and means for receiving signals from said Doppler crystal means intermediate successive pulses.

6. A system as recited in claim 3 wherein said perfusion tube means includes a lumen extending between said distal and proximal ends for enabling the injection of a therapeutic agent to the occluded vessel.

7. A system as recited in claim 6 wherein said lumen additionally carries said conductor means.

8. A system as recited in claim 6 wherein said perfusion tube means includes a second lumen for carrying said conductor means.

9. A system as recited in claim 6 wherein said perfusion tube means comprises a guidewire means having a plurality of apertures proximate the distal end thereof for allowing the passage of a therapeutic agent into the vessel, said transducer means being located distally of said apertures.

10. A system as recited in claim 6 wherein said perfusion tube means includes a catheter means having a plurality of apertures proximate the distal end thereof for allowing the passage of a therapeutic agent into the vessel, said transducer means being located distally of said apertures.

11. A system as recited in claim 1 wherein said announcing means includes means for generating an audio signal to announce the onset of blood flow.

12. A system as recited in claim 1 wherein said announcing means includes means for generating a visual signal to announce the onset of blood flow.

13. A system as recited in claim 1 wherein said announcing means includes transmitter means for broadcasting an encoded signal when said comparing means indicates the onset of blood flow in the vessel and remote receiver means responsive to said broadcast signal for announcing the onset of blood flow remotely to the patient.

14. A system as recited in claim 13 wherein said announcing means includes means for generating an audio signal to announce the onset of blood flow.

15. A system as recited in claim 13 wherein said announcing means includes means for generating a visual signal to announce the onset of blood flow.

16. A method for reperfusing a vessel occluded by a thrombosis using a lytic agent comprising the steps of:
   A. positioning the distal end of a perfusion tube with a flow sensor means into the vessel,
   B. administering the lytic agent in a continuous fashion through the perfusion tube into the vessel from the proximal end thereof,
   C. continuously energizing and monitoring the flow sensor means to determine blood flow rate through the vessel parallel to and past said perfusion tube means,
   D. announcing the onset of blood flow through the vessel above a predetermined flow rate, and
   E. discontinuing the administration of the lytic agent in response to said announcement.

17. A method as recited in claim 16 wherein the flow sensor means comprises ultrasonic transducer means positioned at the distal end of the perfusion tube for directing ultrasonic energy parallel to the perfusion tube and said energizing and monitoring uses Doppler information derived from the transducer means for determining the blood flow rate through the vessel parallel to and past the distal end of the perfusion tube and for comparing the measured blood flow rate with the predetermined blood flow rate thereby to enable said announcement.

18. A method as recited in claim 17 wherein said transducer means includes a Doppler crystal means and said energizing and monitoring causes the Doppler crystal means to transmit energy and receive energy.

19. A method as recited in claim 18 wherein the Doppler crystal means includes first and second crystals, said energizing and monitoring continuously driving the first crystal and receiving signals from the second crystal.

20. A method as recited in claim 18 wherein said energizing and monitoring drives the Doppler crystal means with discrete energy pulses and receives signals from the crystal intermediate the driving pulses.

21. A method as recited in claim 17 wherein said announcement includes broadcasting an encoded signal upon the onset of blood flow in the vessel and remotely receiving the broadcast signal for announcing the onset of blood flow at a location that is remote to the patient.

22. A method as recited in claim 21 wherein said announcement includes generating an audio signal to provide the announcement of the onset of blood flow at the remote location.

23. A method as recited in claim 21 wherein said announcement includes generating a visual signal to provide the announcement of the onset of blood flow at the remote location.

24. A method as recited in claim 16 wherein said announcement includes generating an audio signal.

25. A method as recited in claim 16 wherein said announcement includes generating a visual signal.

* * * * *